United States Patent [19]

Lloyd et al.

[11] 4,207,897
[45] Jun. 17, 1980

[54] CRYOSURGICAL PROBE

[75] Inventors: John W. Lloyd, The Gate House, Eynsham, Oxfordshire, England; David E. Wild, Crawley; Humphry R. Evatt, Stockbridge, both of England

[73] Assignees: Spembly Limited, Hampshire; John W. Lloyd, Oxfordshire, both of England; part interest to each

[21] Appl. No.: 815,290

[22] Filed: Jul. 13, 1977

[30] Foreign Application Priority Data

Jul. 21, 1976 [GB] United Kingdom ............... 30351/76

[51] Int. Cl.² ........................ A61B 17/36; A61F 7/00; A61M 7/00
[52] U.S. Cl. .............................. 128/303.1; 128/400; 128/DIG. 27; 128/786
[58] Field of Search ................... 128/303.1, 254, 255, 128/256, 257, 399, 400, 401, 405, 419 R, 420, 418, 421, 422, 2.1 E, 2.1 Z

[56] References Cited

U.S. PATENT DOCUMENTS

| 1,948,075 | 2/1934 | Miyaoka | 174/89 |
| 3,298,371 | 1/1967 | Lee | 128/400 |
| 3,507,283 | 4/1970 | Thomas | 128/303.1 |
| 3,682,162 | 8/1972 | Colyer | 128/2.1 R |

FOREIGN PATENT DOCUMENTS

| 956868 | 1/1957 | Fed. Rep. of Germany | 128/2 R |
| 2548262 | 7/1976 | Fed. Rep. of Germany | 128/2.1 Z |
| 2289157 | 5/1976 | France | 128/2.1 Z |

Primary Examiner—Robert W. Michell
Assistant Examiner—Thomas J. Wallen
Attorney, Agent, or Firm—Shapiro and Shapiro

[57] ABSTRACT

A cryosurgical probe is adapted for the freezing of a nerve and is fitted with an electrode at its tip for electrical stimulation of the nerve, to enable the surgeon to know when the probe tip has been correctly placed in proximity to a particular nerve which it is desired to freeze.

9 Claims, 4 Drawing Figures

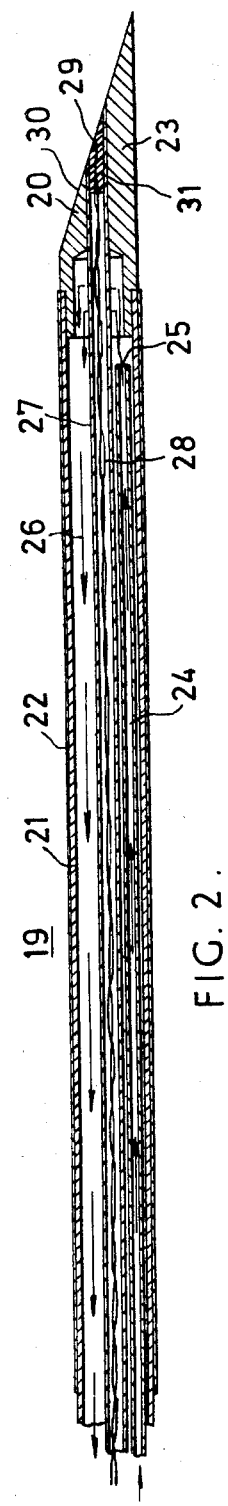
FIG. 2.
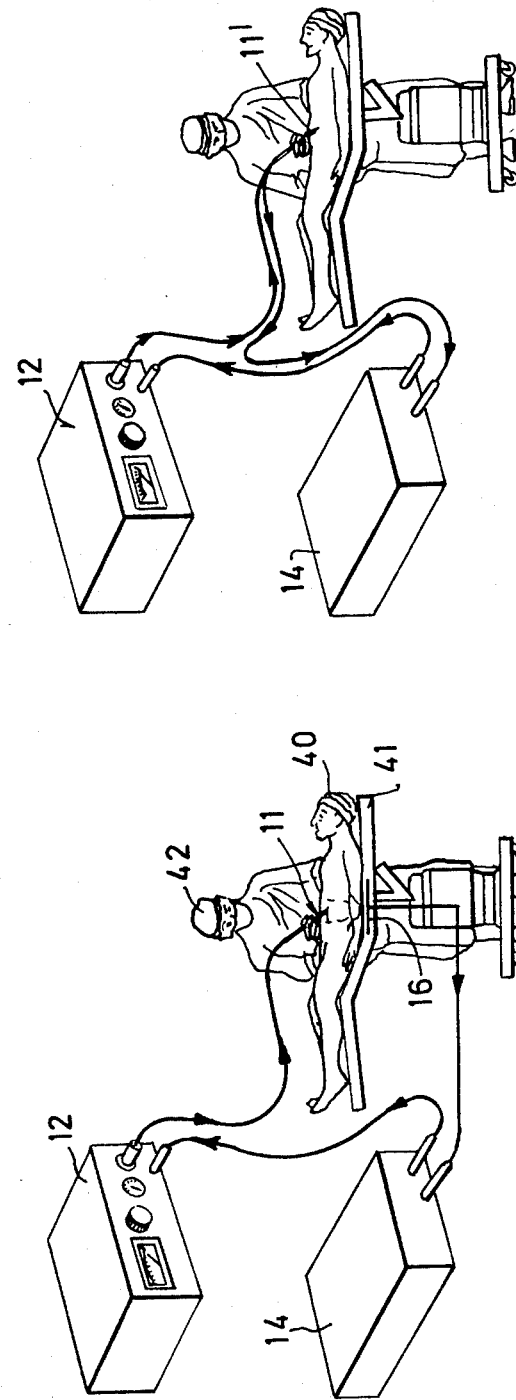
FIG. 3.
FIG. 4.
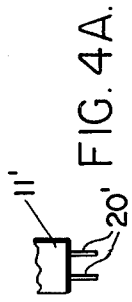
FIG. 4A.

CRYOSURGICAL PROBE

BACKGROUND OF THE INVENTION

Field of the Invention

This invention relates to cryosurgery, which is the use of freezing in surgery, and in particular to the freezing of nerves.

SUMMARY

In its broadest aspect, the invention is a cryosurgical probe equipped with nerve-stimulating means.

From another aspect, the invention is a cryosurgical probe comprising a hollow stem of which one end is adapted to be connected to a source of cooling fluid and to exhaust and of which the other end is closed and is formed as a tip of thermally conductive material adapted to be cooled by means of the cooling fluid, which in use flows along the stem; whereby localised cooling of animal tissue in a part of a living animal (human or otherwise) can be effected by application of the tip to the tissue; the tip including, or being formed as, at least one exposed electrode; said at least one exposed electrode being electrically connectible to an electrical source for application of an electrical stimulus to the tissue in the vicinity of the electrode.

Preferably the probe is adapted to be used with a cooling fluid in the form of the gas or vapour boiled off from liquified gas having a boiling point substantially below normal ambient temperature at normal atmospheric pressure, and is adapted to be cooled at least partly due to the Joule-Thompson effect upon expansion of the gas or vapour inside the stem.

The said exhaust may be directly into atmosphere (if the nature of the fluid permits) or ducted away.

Preferably the electrode and conductor are respectively a single electrode and a single conductor and the probe is adapted to be used in conjunction with a separate electrode applied in use to another part of the animal.

Preferably the stem has a thermally and electrically insulating outer layer, elsewhere than at the tip, for example, a layer of polytetrafluoroethylene (P.T.F.E.).

Preferably the tip incorporates the measuring junction of a thermocouple, and electrical leads of the thermocouple extend along the stem. One of said leads may be the said electrical conductor connected to the said electrode.

A preferred application of the invention is to a method of chilling or freezing a neurone, in which the electrical stimulus enables a surgeon or anaesthetist to locate the neurone and/or determine the extent of the chilling or freezing of the neurone, by observing the animals's response to the stimulus.

Preferably the tip is sharp so that it can be intruded beneath the surface of the tissue, whether it be an internal surface exposed by surgery or accident or an external surface, e.g. skin. However, the tip need not be sharp if the probe is required only for internal use during an operation or for external use.

BRIEF DESCRIPTION OF THE DRAWINGS

FIG. 2 is a section through a front end portion of the stem of the probe of FIG. 1;

FIG. 3 illustrates use of the apparatus of FIG. 1 on a patient;

FIG. 4 illustrates use of a modified apparatus on a patient; and

FIG. 4A illustrates the tip of a probe used in the modified apparatus.

DESCRIPTION OF THE PREFERRED EMBODIMENT

Figure 1:
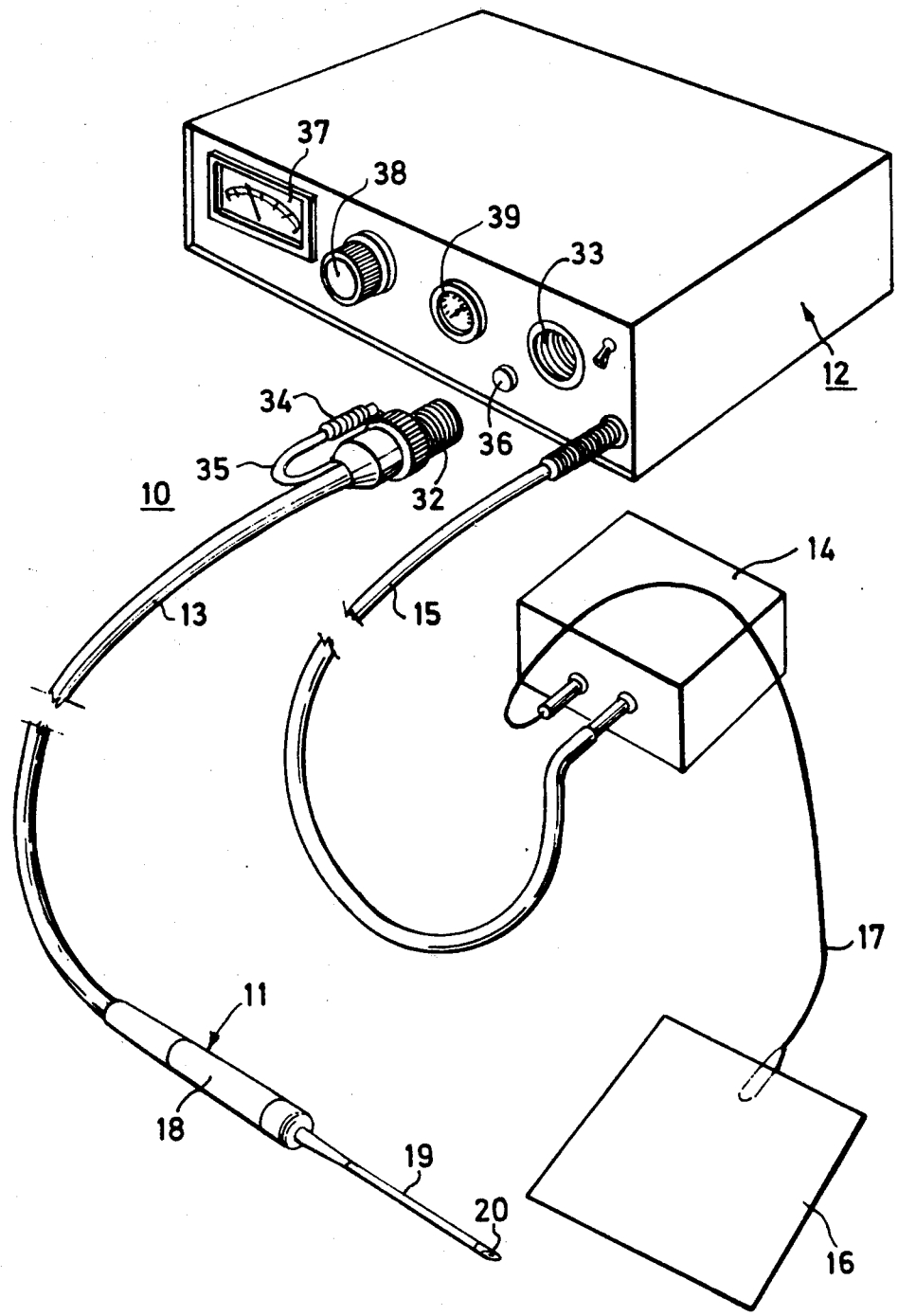
FIG. 1 illustrates a cryosurgical probe and associated apparatus embodying the invention.

Referring to FIGS. 1, 2 and 3, the illustrated apparatus 10 comprises a cryosurgical probe 11, a control unit 12, a flexible lead 13 which connects the probe 11 to the control unit 12 and which contains ducts (not shown) for the supply of cooling fluid to the probe and for return flow of the cooling fluid and electrical leads. The apparatus 10 also comprises a nerve-stimulator unit 14 which is connected to the control unit 12 by a flexible electrical lead 15 and is connected to an electrode 16 by a lead 17.

The cryosurgical probe 11 comprises a handle 18 connected to a hollow stem 19. The end (not shown) inside the handle 18 of stem 19 is adapted to be connected to a source (not shown) of cooling fluid and to exhaust, via the lead 13. The other end 20 of stem 19 is closed and is formed as a tip of thermally conductive material adapted to be cooled by means of the cooling fluid, which in use flows along the stem 19.

Referring more particularly to FIG. 2, the stem 19 comprises a tube 21 of stainless steel, covered with a layer 22 of P.T.F.E. (in the form available under the Registered Trade Mark "TEFLON"). Inserted in the front end of the tube 21 is a stainless steel insert 23, sharpened to an 18° long bevel as shown, to form the tip 20 of the stem 19. Inside the tube 21 is a stainless steel gas inlet tube 24, formed at its front end with an expansion orifice 25. Cooling fluid issuing from the orifice 25 serves to cool the stainless steel insert 23, the cooling fluid returning along the interior of the tube 21, outside the tube 24, as illustrated by arrows 26. Another stainless steel tube 27 contains two electrical leads 28, leading to a thermocouple junction 29 at the face 30 of the bevel, the thermocouple junction 29 being electrically insulated from the stainless steel insert 23 by a plug 31 of plastics insulating material.

The stainless steel insert 23 forms an exposed electrode at the tip 20 of stem 19, and being in direct contact with the stainless steel tube 21, is electrically connected via the tube 21, lead 13, unit 12 and lead 15 to the unit 14, which is adapted to supply electrical pulses to the electrode formed by insert 23 as an electrical stimulus to the animal tissue (see FIG. 3) in the vicinity of the insert 23. The layer 22 of P.T.F.E. forms a thermally and electrically insulating outer layer around the stem 19, elsewhere than at the tip 20.

The lead 13 is provided with a screw-threaded coupling 32, engageable in a socket 33 in the control unit 12, for the supply and exhaust of cooling fluid. An electrical connector 34 is connected by a jumper lead 35 to the connector 32 and is engageable in a socket 36 in the control unit 12.

The illustrated apparatus is used with a bottle (not shown) of cooling fluid in the form of liquified gas such as liquid carbon dioxide or liquid nitrous oxide, which has a boiling point substantially below normal ambient temperature at normal atmospheric pressure. In use, the bottle of liquid gas (not shown) is connected by means not shown to the control unit 12, whence gas or vapour boiled off from the liquid gas flows along lead 13 into the tube 24 inside stem 19, issuing from the orifice 25 inside the stem 19 and having the effect of cooling the tip (for example down to a temperature of −40° C.) at least partly due to the Joule-Thompson effect upon expansion of the gas or vapour inside the stem 19. The temperature in the region of the face 30 of the bevelled tip 20 is detected by the thermocouple junction 29 and can be read on a meter 37 on the control unit 12. The rate of flow of cooling vapour along the tube 24 can be controlled by means of a rotary control knob 38 on the control unit 12, for controlling the temperature of the tip 20. It will be appreciated that the temperature indicated by the meter 37 is at best only the temperature of the stem tip 20, not the temperature of the tissue to which the stem tip 20 has been applied, but nevertheless the meter 37 provides a useful indication of the effectiveness of the probe 11 for cooling the tissue, and can show when the tip 20 has cooled down sufficiently for use, as well as (more importantly) indicating when cooling is not as rapid or effective as usual, due to some malfunction. A pressure gauge 39 on control unit 12 indicates the supply pressure of the cooling gas or vapour.

In use, referring to FIG. 3, the patient (indicated by reference 40) is laid on an operating table 41, in electrical contact with the electrode 16 as shown. The surgeon or anaesthetist (indicated by reference 42) may then intrude the probe tip 20 into the patient, the tip 20 being sufficiently sharp for intrusion without unacceptable traumatic effect on the patient. By means of the nerve stimulator unit 14, electrical pulse stimuli are applied to the patient via the stainless steel insert 23. If the probe tip 20 is close to a nerve which it is desired to freeze by means of the probe 11, the electrical stimulus has an observable effect upon the patient, for example, causing twitching of a particular muscle, whereby the surgeon or anaesthetist can ascertain the proximity or otherwise of the probe tip 20 to the desired nerve. When the surgeon or anaesthetist is reasonably sure that the probe tip 20 is as near as possible to the nerve, from observing the effect of the electrical stimulus on the patient, the cooling fluid can be switched on to effect freezing of the nerve, during which time the probe 11 is held motionless with the probe tip 20 in close proximity to the nerve. During this time, progressively decreasing reaction of the patient to the electrical stimulus will indicate freezing of the nerve, or neurone. When the surgeon or anaesthetist is satisfied that sufficient freezing of the nerve or neurone has taken place, the flow of cooling fluid is cut off and the tip 20 is allowed to thaw. When the tip 20 has thawed sufficiently, as indicated by the meter 37, the probe 11 may be withdrawn from the patient. It will be appreciated that the probe 11 must not be moved until it has thawed, because the frozen tip 20 will stick to adjacent tissue in the patient. Preferably, a first freezing and thawing cycle is followed by a second such cycle, the freezing period of each said cycle being from 1½ to 3 minutes, to ensure freezing of the nerve.

The pulse repetition rate of the nerve stimulator unit 14 is one pulse per second approximately, the pulse voltage being selectively variable. Instead of nitrous oxide, the liquified gas may be carbon dioxide.

Instead of observing muscular contraction of the patient, if the patient is conscious the surgeon or anaesthetist may rely upon verbal communication with the patient. It is important for the area of contact with the patient of electrode 16 to be large enough to avoid stimulating the patient except at the location of the probe tip 20.

Gas pressure may be around 600 pounds per square inch, in which case the minimum temperature obtainable at the probe tip bevel face 30 is −80° C. in air or −60° C. within the patient, the time to reach minimum temperature being approximately 45 seconds, a typical freeze period 1½ to 3 minutes, a typical rewarm time approximately 1 minute. The length of the probe stem 19 is preferably about 100 millimetres, its diameter 1.8 millimetres.

The nerve stimulator unit 14 may be a "Welcomme-Burroughs peripheral nerve stimulator unit", with a maximum output of 200 volts, giving a substantially instantaneous voltage rise to a preset level, followed by exponential decay with a time constant of 0.1 milliseconds, independent of load. The stimulator unit 14 is also capable of delivering a tetanic stimulation with the same voltage waveform with spikes up to 200 volts with a 28 millisecond repetition rate (i.e. 35 Hz) at a 20 Kilohm output impedance.

In the modified apparatus illustrated in FIG. 4, the same control unit 12 and stimulator unit 14 are used as in FIG. 3. However, a modified cryosurgical probe 11' has a modified probe tip (FIG. 4a) with two spaced-apart exposed electrodes 20' electrically connected as shown to opposite terminals of the nerve stimulator unit 14, dispensing with the need for the electrode 16 of FIG. 3. Because the electrodes 20' at the tip of probe 11' of FIG. 4A are relatively close together, compared with the distance between the probe tip 20 and electrode 16 of FIG. 3, a much higher voltage is required for stimulating the patient.

In FIGS. 3 and 4, the electrical connections are shown purely diagrammatically.

We claim:

1. A cryosurgical device comprising a probe having a hollow stem, one end of the stem having means adapted to be connected to a source of cooling fluid and to exhaust, the opposite end of the stem being closed and having a thermally conductive tip adapted to be cooled by means of the cooling fluid which in use flows along the stem, whereby human or animal tissue at the tip may be cooled, said tip providing an exposed electrode, a further electrode separate from said probe and adapted to be applied to a part of said human or animal separate from the tissue to be cooled, and means for applying electrical nerve-stimulating voltages between the said electrodes sufficient to cause an observable muscle response in the human or animal.

2. A device as claimed in claim 1, wherein the probe is adapted to be used with a cooling fluid in the form of a gas or vapour boiled off from a liquefied gas having a boiling point substantially below normal ambient temperature at normal atmospheric pressure.

3. A device as claimed in claim 2, wherein the probe is adapted to be cooled at least partly due to the Joule-Thomson effect upon expansion of the gas or vapour inside said stem.

4. A device as claimed in claim 1, wherein the stem has a thermally and electrically insulating outer layer, elsewhere than at the tip.

5. A device as claimed in claim 4, wherein the tip incorporates the measuring junction of a thermocouple and electrical leads of the thermocouple extend along the stem.

6. A device as claimed in claim 1, wherein the tip is sharp so that it can be intruded beneath the surface of the tissue.

7. A device as claimed in claim 1, wherein the means for applying electrical nerve-stimulating voltages produces voltage pulses.

8. A cryosurgical device comprising a probe having a hollow stem, one end of the stem having means adapted to be connected to a source of cooling fluid and to exhaust, the opposite end of the stem being closed and having a thermally conductive tip adapted to be cooled by means of the cooling fluid which in use flows along the stem, whereby human or animal tissue at the tip may be cooled, said tip having a pair of exposed electrodes, and means for applying electrical nerve-stimulating voltages between the said electrodes sufficient to cause an observable muscle response in the human or animal.

9. A device as claimed in claim 8, wherein the means for applying electrical nerve-stimulating voltages produces voltage pulses.

* * * * *